(12) United States Patent
Dockner et al.

(10) Patent No.: US 8,455,689 B2
(45) Date of Patent: Jun. 4, 2013

(54) PROCESS FOR PREPARING SUBSTITUTED BIPHENYLANILIDES

(75) Inventors: Michael Dockner, Cologne (DE); Heiko Rieck, Burscheid (DE); Wahed Ahmed Moradi, Monheim (DE); Norbert Lui, Odenthal (DE)

(73) Assignee: Bayer CropScience AG, Monheim (DE)

( * ) Notice: Subject to any disclaimer, the term of this patent is extended or adjusted under 35 U.S.C. 154(b) by 138 days.

(21) Appl. No.: 12/991,265

(22) PCT Filed: Apr. 24, 2009

(86) PCT No.: PCT/EP2009/003005
§ 371 (c)(1),
(2), (4) Date: Nov. 5, 2010

(87) PCT Pub. No.: WO2009/135598
PCT Pub. Date: Nov. 12, 2009

(65) Prior Publication Data
US 2011/0092736 A1    Apr. 21, 2011

Related U.S. Application Data

(60) Provisional application No. 61/130,671, filed on Jun. 2, 2008.

(30) Foreign Application Priority Data

May 9, 2008  (EP) ...................................... 08155977

(51) Int. Cl.
*C07C 233/05*    (2006.01)
(52) U.S. Cl.
USPC .............................................. 564/221; 568/6
(58) Field of Classification Search
CPC ..................................................... C07C 233/02
USPC .............................................. 564/221; 568/6
See application file for complete search history.

(56) References Cited

U.S. PATENT DOCUMENTS

| | | | |
|---|---|---|---|
| 6,958,330 B1 | 10/2005 | Audia et al. | |
| 7,329,633 B2 | 2/2008 | Dunkel et al. | |
| 7,750,186 B2 | 7/2010 | Jörges et al. | |
| 7,772,446 B2 | 8/2010 | Engel et al. | |
| 2011/0003999 A1 | 1/2011 | Dockner | |

FOREIGN PATENT DOCUMENTS

| | | |
|---|---|---|
| DE | 10 2004 041 531 A1 | 3/2006 |
| DE | 10 2006 036 222 A1 | 2/2008 |
| WO | WO 03/070705 A1 | 8/2003 |
| WO | WO 2006/092429 A1 | 9/2006 |

OTHER PUBLICATIONS

Ishikawa, T., et al., "Anomalous Substituent Effects in the Bischler-Napieralski Reaction of 2-Aryl Aromatic Formamides," *J. Org. Chem.* 65:9143-9151, American Chemical Society, United States (2000).
International Search Report of International Application No. PCT/EP2009/003005, European Patent Office, Rijswijk, Netherlands, mailed Oct. 1, 2009.
English language Abstract of German Patent Publication No. DE 10 2006 036 222 A1, European Patent Office, espacenet database—Worldwide, (2008).
Tsang, W.C.P., et al., "Combined C-H Functionalization / C-N Bond Formation Route to Carbazoles," *Journal of the American Chemical Society* 127(42):S1-S19, American Chemical Society, United States (2005).

*Primary Examiner* — Shailendra Kumar
(74) *Attorney, Agent, or Firm* — Sterne, Kessler, Goldstein & Fox P.L.L.C.

(57) ABSTRACT

The present invention relates to a process for preparing substituted biphenylanilides of the formula I

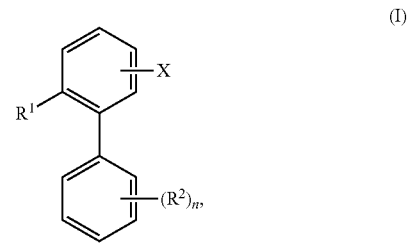

wherein $R^1$ is a protected amino group
which comprises reacting a compound of formula II

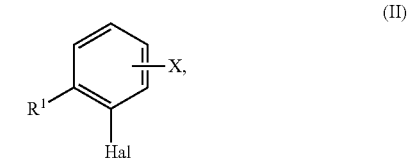

in the presence of a base and of a palladium catalyst
in a solvent, with an organoboron compound of formula (III)

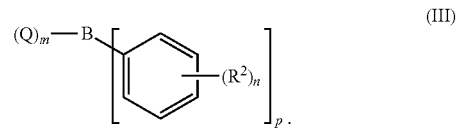

14 Claims, No Drawings

PROCESS FOR PREPARING SUBSTITUTED BIPHENYLANILIDES

This application is a 371 of PCT/EP09/03005, filed Apr. 24, 2009.

The present invention relates to a process for preparing substituted biphenylanilides of the formula I

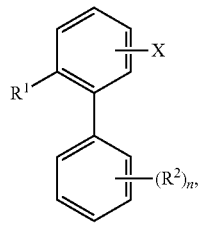
(I)

wherein
X is hydrogen fluorine or chlorine;
$R^1$ is a protected amino group;
$R^2$ is cyano, nitro, halogen, $C_1$-$C_6$-alkyl, $C_1$-$C_6$-alkenyl, $C_1$-$C_6$-alkynyl, $C_1$-$C_6$-alkoxy, $C_1$-$C_6$-haloalkyl, ($C_1$-$C_6$-alkyl)carbonyl or phenyl;
n is 1, 2 or 3, where in case that n is 2 or 3, the $R^2$ radicals may also be different,
which comprises reacting a compound of formula II

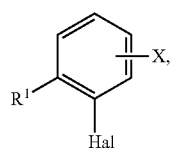
(II)

in which Hal is halogen and X is as defined above, in the presence of a base and of a palladium catalyst selected from the group of:
a) palladium-triarylphosphine or -trialkylphosphine complex with palladium in the zero oxidation state,
b) salt of palladium in the presence of triarylphospine or trialkylphosphine as a complex ligand or
c) metallic palladium, optionally applied to support, in the presence of triarylphosphine or trialkylphosphine,
in a solvent, with an organoboron compound of formula (III)

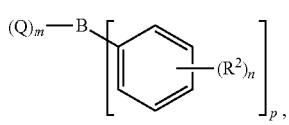
(III)

which is selected from the group consisting of:
(i) boronic acids of formula (III)
wherein
m is 2,
p is 1,
Q is a hydroxyl-group,
$R^2$ and n are as defined above,
or the anhydrides, dimers or trimers formed thereof;

(ii) boronic acid derivatives of formula (III), wherein
m is 2,
p is 1,
each Q is independently selected from F, Cl, Br, I, $C_{1-4}$-alkyl-, $C_{6-10}$-aryl, $C_{1-4}$-alkoxy- and $C_{6-10}$-aryloxy-residues,
$R^2$ and n are as defined above;
(iii) borinic acids of formula (III),
wherein
m is 1,
p is 2,
Q is selected from OH, F, Cl, Br, I, $C_{1-4}$-alkyl-, $C_6$-$C_{10}$-aryl-, $C_{1-4}$-alkoxy- and $C_{6-10}$-aryloxy-residues,
$R^2$ and n are as defined above;
(iv) cyclic boronic acid esters of formula (III),
wherein
m is 2,
p is 1,
each Q is independently selected from $C_{1-4}$-alkoxy residues which together with the boron atom they are attached to form a 5- or 6-membered ring which may be substituted by $C_{1-4}$-alkyl-residues,
$R^2$ and n are as defined above;
(v) boronates of formula (III)
wherein
m is 3,
p is 1,
$R^2$ and n are as defined above,
each Q is independently selected from OH, F, Cl, Br, I, $C_{1-4}$-alkyl-, $C_{6-10}$-aryl-, $C_{1-4}$-alkoxy- and $C_{6-10}$-aryloxy-residues,
and wherein the negative charge of the boronate anion is compensated by a cation;
(vi) triarylboranes of formula (III),
wherein
m is 0,
p is 3,
$R^2$ and n are as defined above;
(vii) tetraarylborates of formula (III);
wherein
m is 0,
p is 4,
$R^2$ and n are as defined above,
and wherein the negative charge of the boronate anion is compensated by a cation;
where the triarylphosphines or trialkylphosphines used may be substituted.

Tsutomu Ishikawa et al, JOCS, Vol. 65, No. 26, 2000, 9143-9151 teaches the synthesis of phenolic 2-arylformanilides by Suzuki coupling between protected arylboronic acids and 2-bromoformanilide followed by methylation and deprotection. However, the present invention does not use protected arylboronic acids.

Tetrahedron Lett. 32, page 2277 (1991) states that the coupling reaction between phenylboronic acid and chlorobenzene with use of the [1,4-bis(diphenylphosphine)-butane]palladium(II) dichloride catalyst proceeds with a yield of only 28%.

EP-A 0 888 261 discloses a process for preparing nitrobiphenyls by reacting chloronitro-benzenes with a phenylboronic acid in the presence of a palladium catalyst and of a base. In this process, a very high catalyst concentration is necessary.

WO 2006/092429 and WO 2007/138089 each pertain to a process for preparing substituted biphenyls by coupling substituted diphenylborinic acids with dihaloarylcompounds in presence of a palladium catalyst. The yields of the coupling reaction described therein are still unsatisfactory and the formation of undesirable side products, such as dehalogenation products, triaryls and polychlorinated biphenyls (PCB) can be observed.

It was therefore an object of the present invention to provide an economically viable process which can be implemented on the industrial scale for selectively preparing substituted biphenyl-anilides in high yields.

Accordingly, the process defined at the outset has been found.

It has surprisingly been found that the Suzuki coupling of amino-substituted aryl halides can be performed under milder reaction conditions, if the amino group of the aryl halide is protected by a protection group. Consequently, the process according to the present invention leads to higher yields due to a reduced side product formation.

Organoboron Compounds

The organoboron compounds which can be used in the process according to the present invention:
(i) Boronic acids of formula (III)

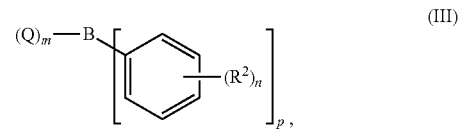

wherein
m is 2,
p is 1,
each Q is a hydroxyl-group,
$R^2$ and n are as defined above,
can be obtained by conversion of arylmagnesium halides with trialkylborates in preferably in THF as a solvent. In order to repress the formation of arylborinic acids it is necessary to avoid the excess of either of the reagents and to carry our the reaction at low temperatures of $-60°$ C. as it is described in R. M. Washburn et al. Organic Syntheses Collective Vol. 4, 68 or in Boronic Acids, Edited by Dennis G. Hall, Wiley-VCH 2005, p. 28ff and references cited therein.

Boronic acids, which can be used according to the present invention, are exemplified by the following compounds: (2,3-difluorophenyl)boronic acid, (3,4-di-fluorophenyl) boronic acid, (2,3-dichloro-phenyl)boronic acid and in particular (3,4-dichlorophenyl)boronic acid and (4-chlorophenyl)boronic acid.

(ii) Boronic acid derivatives of formula (III), wherein
m is 2,
p is 1,
each Q is independently selected from F, Cl, Br, I, $C_{1-4}$-alkyl-, $C_{6-10}$-aryl-, $C_{1-4}$-alkoxy- and $C_{6-10}$-aryloxy-residues,
$R^2$ and n are as defined above;

(iii) Bonnie acids of formula (III),
wherein
m is 1,
p is 2,
Q is selected from OH, F, Cl, Br, I, $C_{1-4}$-alkyl-, $C_{6-10}$-aryl-, $C_{1-4}$-alkoxy- and $C_{6-10}$-aryloxy-residues, in a preferred embodiment $Q^1$ is a hydroxyl residue;
$R^2$ and n are as defined above;
is obtained by reaction of optionally substituted phenylmagnesium chloride V with trialkyl borate, preferably trimethyl borate, in tetrahydrofuran as a solvent according to WO 2007/138089 as described by scheme 1.

Scheme 1

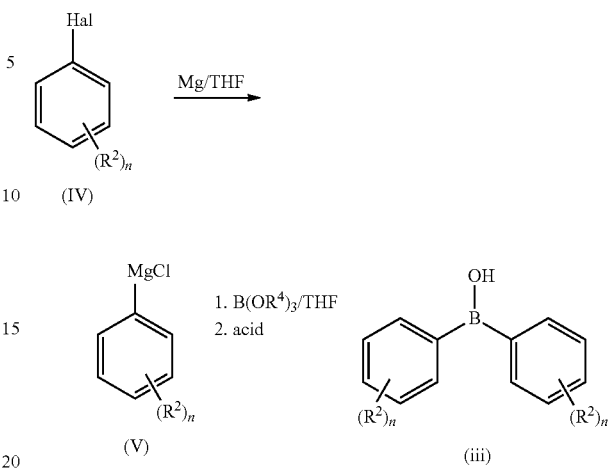

$R^4$ is $C_1$-$C_4$-alkyl, preferably methyl.

Hal is Cl, Br, I.

Preference is given to starting from diphenylborinic acids of the formula (iii) in which m is 1, p is 2, Q is OH and $R^2$ and n are as defined above.

Further starting materials are diphenylborinic acids (iii) in which n is 1 or 2, in particular 2. Particularly preferred are diphenylborinic acids (iii) which are substituted in the 3- and 4-position or in 4-position only.

Borinic acids which can be used according to the present invention, are exemplified by the following compounds:

di(2,3-difluorophenyl)borinic acid, di(3,4-di-fluorophenyl)borinic acid, di(2,3-di-chlorophenyl)borinic acid and in particular di(3,4-dichlorophenyl)borinic acid and (4-chlorophenyl)borinic acid.

Essential for a high yield of diphenylborinic acid (iii) is the use of only 0.7 eq. of trialkyl borate based on the substituted chlorobenzene (IV) used. Use of 1.1 eq. of trialkyl borate gives rise to phenylboronic acid as described in EP-A 0 888 261.

The reaction temperature in this process stage ranges for example from $-20$ to $100°$ C., from 20 to $80°$ C. or from 40 to $60°$ C.

(iv) Cyclic boronic acid esters of formula (III),
wherein
m is 2,
p is 1,
each Q is independently selected from $C_{1-4}$-alkoxy residues which together with the boron atom they are attached to form a 5- or 6-membered ring which may be substituted by $C_{1-4}$-alkyl-residues;
$R^2$ and n are as defined above;
can be obtained as described in Boronic Acids, Edited by Dennis G. Hall, Wiley-VCH 2005, p. 28ff and references cited therein.

Cyclic boronic acid esters, which can be used according to the present invention, are exemplified by compounds according to the following formulas (iv-1) to (iv-3)

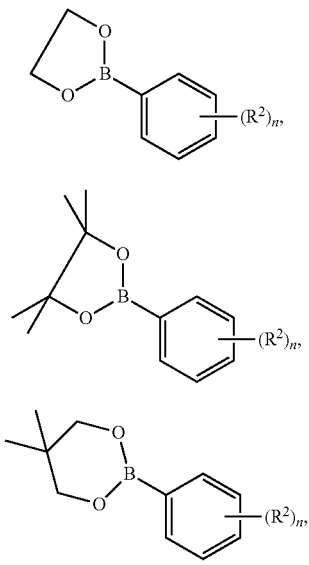

wherein $R^2$ and n are as defined above.

(v) Boronates of formula III
wherein
m is 3,
p is 1,
$R^2$ and n are as defined above;
each Q is independently selected from OH, F, Cl, Br, I, $C_{1-4}$-alkyl-, $C_{6-10}$-aryl-, $C_{1-4}$-alkoxy- and $C_{6-10}$-aryloxy-residues, in a preferred embodiment of the present invention $Q^1$, $Q^2$ and $Q^3$ are each hydroxyl residues,
and wherein the negative charge of the boronate anion is compensated by a cation as indicated by the following formula (iv-1).

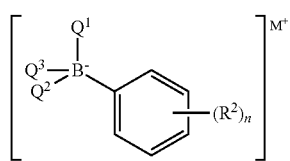

The cation ($M^+$) is for example selected from the group consisting of ammonium-($NH_4^+$), alkaline- or earth alkaline metal cations, such as $Na^+$, $K^+$, $Li^+$, $Mg^{2+}$, $Ca^{2+}$.
The boronates (v) can be obtained as described in Serwatowski et al. Tetrahedron Lett. 44, 7329 (2003).

(vi) Triarylboranes of formula (III),
wherein
m is 0,
p is 3,
$R^2$ and n are as defined above.
The triarylboranes (vi) can be obtained as described in H. C. Brown et al J. Organomet. Chem. 73, 1 (1988) and in H. C. Brown et al., "Borane reagents", Harcourt Brace Jovanovich, Publishers, (1988).

(vii) Tetraarylborates of formula (III),
wherein
m is 0,
p is 4,
$R^2$ and n are as defined above;
and wherein the negative charge of the boronate anion is compensated by a cation which is for example selected from the group consisting of ammonium-($NH_4^+$), alkaline- or earth alkaline metal cations, such as $Na^+$, $K^+$, $Mg^{2+}$, $Ca^{2+}$.

The tetraarylborates (vii) can be obtained as described in J. Serwatowski et al. Tetrahedron Lett. 44, 7329 (2003).

Suzuki Coupling

According to the present invention substituted biphenylanilides of the formula I can be obtained highly selective and with high yields.

When the amino group of the aryl halide of formula (II) is protected by a protection group, the Suzuki coupling can be performed under milder reaction conditions. Consequently, the formation of undesirable side products, such as dehalogenation products, triaryls and polychlorinated biphenyls (PCB) is significantly reduced.

Protection group in this context denotes any kind of chemical group which can be used in order to modify the amino group of the aryl halide of formula (II) during the Suzuki coupling step and which can be removed after the coupling from the substituted biphenylanilide of formula (I), for instance by reacting it with an aqueous acid, giving back the original amine. This step is called deprotection.

Protection groups which can generally be employed for the protection of amine groups are exemplified by the groups:

Carbobenzyloxy (Cbz) group which is formed by reacting an amine with benzyl chloroformate and a weak base. It is used to protect amines from electrophiles. The protected amine can be deprotected by catalytic hydrogenation or treatment with HBr. The Carbobenzyloxy (Cbz) group are known in the prior art, for instance from Max Bergmann, Leonidas Zervas (1932). "Über ein allgemeines Verfahren der Peptid-Synthese". Berichte der deutschen chemischen Gesellschaft 65 (7): 1192-1201. doi:10.1002/cber.19320650722 or J. Clayden, N. Greeves, S. Warren, P. Wothers, "Organic Chemistry", Oxford University Press, 2001 tert-Butyloxycarbonyl (BOC) group which is a reagent widely used in organic synthesis and well known in the prior art, for instance from Wakselman, M. "Di-t-butyl Dicarbonate" in Encyclopedia of Reagents for Organic Synthesis (Ed: L. Paquette) 2004, J. Wiley & Sons, New York. This carbonate ester reacts with amines to give N-tert-butoxycarbonyl or so-called t-BOC derivatives. These derivatives do not behave as amines, which allows certain subsequent transformations to occur that would have otherwise affected the amine functional group. The t-BOC can later be removed from the amine using acids. Thus, t-BOC serves as a protective group, for instance in solid phase peptide synthesis. It is stable to most bases and nucleophiles. The Boc group can be added to the amine under aqueous conditions using di-tert-butyl dicarbonate in the presence of a base such as sodium bicarbonate. Protection of the amine can also be accomplished in acetonitrile solution using 4-dimethylaminopyridine (DMAP) as the base. Removal of the t-BOC in amino acids can be accomplished with strong acids such as trifluoroacetic acid neat or in dichloromethane, or with HCl in methanol.

9-Fluorenylmethyloxycarbonyl (Fmoc) group which is a widely used protective group that is generally removed from the N terminus of a peptide in the iterative synthesis of a peptide from amino acid units. The advantage of Fmoc is that it is cleaved under very mild basic conditions (e.g. piperidine), but stable under acidic conditions. This allows mild acid labile protecting groups that are stable under basic conditions, such as Boc and benzyl groups, to be used on the side-chains of amino acid residues of the target peptide. This orthogonal protecting group strategy is common in the art of organic synthesis.

Schiff bases (RR″C=N—R′) which are obtained by reacting the amino group with an aldehyde or ketone. Removal of the Schiff base protection group can be accomplished for example by acidic treatment, by hydrogenation with Pd/C/ hydrogen as described in J. Am. Chem. Soc. 1960, 82, 5688 or with hydrazine in ethanol as described in J. Chem. Soc. C, 1969, 1758.

Preferably used are ketones such as acetone, benzophenone or pinakolon or aldehydes such as formaldehyd, acetaldehyd or benzaldehyd.

Acetylamino- and acetacetylamino groups are obtained by reacting the amino group with acetic acid or with acetacetic acid esters. Removal of the groups can be accomplished by acidic treatment In an embodiment of the present invention the amino group of the aryl halide of formula (II) is protected by a Schiff base, by an acetamino- or by an acetacetylamino group.

In this preferred embodiment of the invention
$R^1$ is —NH(CO)$R^3$, —N=CR$^4$R$^5$;
$R^3$, $R^4$, $R^5$ independent from each other represent hydrogen, —CH$_2$—(C=O)—C$_{1-8}$-alkyl, C$_{1-8}$-alkyl, C$_{1-8}$-alkenyl, C$_{1-8}$-alkynyl or C$_{6-18}$-aryl; or wherein
$R^4$, $R^5$ together with the carbon atom they are attached to may form a five- or six-membered ring comprising one, two or three hetero atoms selected from N, O or S;

In another embodiment of the invention the substituted biphenyls prepared by the present process have the following substituents, in each case both individually and in combination.
$R^1$ is —NH(CO)CH$_3$;
$R^2$ is fluorine, chlorine, bromine, more preferably chlorine;
X is hydrogen, fluorine, chlorine, bromine, more preferably fluorine;
n is 1 or 2, preferably 2.

The subsequent homogeneously catalyzed Suzuki biaryl cross-coupling is carried out according to scheme 2.

Scheme 2

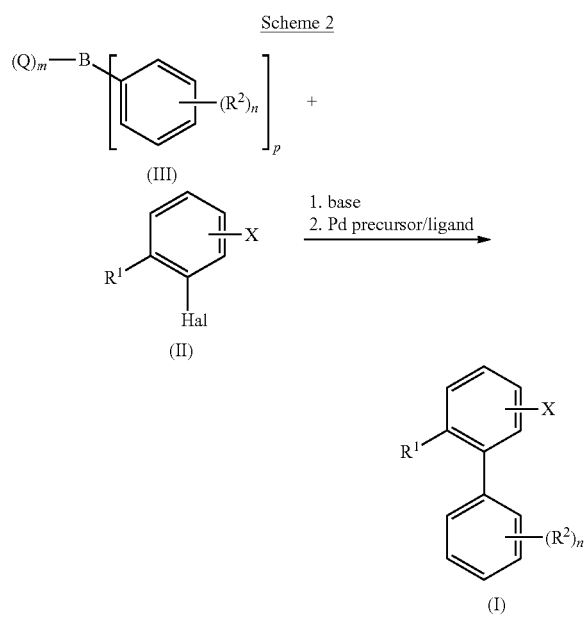

Examples of arylhalides of formula II which can be used according to the present invention are N-(2-bromo-4-fluorophenyl)acetamide, N-(2-chloro-4-fluorophenyl)acetamide, N-(2-bromo-phenyl)acetamide, N-(2-chlorophenyl)acetamide, 2-bromo-N-(propan-2-ylidene)aniline, 2-chloro-N-(propan-2-ylidene)aniline, 2-bromo-4-fluoro-N-(propan-2-ylidene)aniline, 2-chloro-4-fluoro-N-(propan-2-ylidene)aniline, N-(2-chlorophenyl)-3-oxobutanamide, N-(2-bromophenyl)-3-oxobutanamide, N-(2-chloro-4-fluorophenyl)-3-oxobutanamide, N-(2-bromo-4-fluorophenyl)-3-oxobutanamide.

Compounds according to formula (II) can be prepared by reaction of the anilines of formula (IIa) with carboxylic acids, aldehydes or ketones.

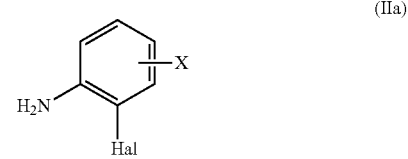

The compound (II) is used, based on the organoboron compound (III) (boron equivalents), normally in an equimolar amount, preferably with an up to 20 percent excess, in particular with an up to 50 percent excess, most particular with an up to 100 percent excess.

Examples of combinations of compounds (II) and (III) according to the present invention are:

Compound (II) is N-(2-bromo-4-fluorophenyl)acetamide 2-bromo-4-fluoro-N-(propan-2-ylidene)aniline and compound (III) is di(3,4-dichlorophenyl)borinic acid.

Compound (II) is N-(2-bromophenyl)acetamide or 2-bromo-N-(propan-2-ylidene)aniline and compound (III) is di(3,4-dichlorophenyl)borinic acid.

Compound (II) is N-(2-bromophenyl)acetamide or 2-bromo-N-(propan-2-ylidene)aniline and compound (III) is (4-chlorophenyl)borinic acid.

The bases used may be organic bases, for example tertiary amines. Preference is given to using, for example, triethylamine or dimethylcyclohexylamine. The bases used are preferably alkali metal hydroxides, alkaline earth metal hydroxides, alkali metal carbonates, alkaline earth metal carbonates, alkali metal hydrogen-carbonates, alkali metal acetates, alkaline earth metal acetates, alkali metal alkoxides and alkaline earth metal alkoxides, in a mixture and in particular individually. Particularly preferred bases are alkali metal hydroxides, alkaline earth metal hydroxides, alkali metal carbonates, alkaline earth metal carbonates and alkali metal hydrogen-carbonates. Especially preferred bases are alkali metal hydroxides, e.g. sodium hydroxide and potassium hydroxide, and also alkali metal carbonates and alkali metal hydrogen-carbonates, e.g. lithium carbonate, sodium carbonate and potassium carbonate. The base is used in the process according to the invention preferably with a fraction of from 100 to 500 mol %, more preferably from 150 to 400 mol %, based on the amount of organoboron compound (III). Suitable palladium catalysts are palladium-ligand complexes with palladium in the zero oxidation state, salts of palladium in the presence of complex ligands, or metallic palladium optionally applied to support, preferably in the presence of complex ligands. Suitable complex ligands are uncharged ligands such as triarylphosphines and trialkylphosphines, which may optionally be substituted in the aryl rings, such as triphenylphosphine (TPP), di-1-adamantyl-n-butylphosphine, tri-tert-butylphosphine (TtBP) or 2-(dicyclohexylphosphino)biphenyl.

Furthermore, the literature has also described further particularly reactive complex ligands from other structural classes, including 1,3-bis(2,6-diisopropylphenyl)-4,5-H2-imidazolium chloride (cf., for example, G. A. Grasa et al. Organometallics 2002, 21, 2866) and tris(2,4-di-tert-butylphenyl) phosphite (cf. A. Zapf et al., Chem. Eur. J. 2000, 6, 1830).

The reactivity of the complex ligands can be enhanced by adding a quaternary ammonium salt such as tetra-n-butylammonium bromide (TBAB) (cf., for example, D. Zim et al., Tetrahedron Lett. 2000, 41, 8199). If required, the water solubility of the palladium complexes can be improved by various substituents such as sulfonic acid or sulfonate salt groups, carboxylic acid or carboxylate salt groups, phosphonic acid, phosphonium or phosphonate salt groups, per-alkylammonium, hydroxyl and polyether groups. Among the palladium-ligand complexes with palladium in the 0 oxidation state, preference is given to using tetrakis-(triphenylphosphine)palladium and additionally tetrakis[tri(o-tolyl)phosphine]palladium. In the salts of palladium which are used in the presence of complex ligands, the palladium is normally present in the two positive oxidation state. Preference is given to using palladium chloride, palladium acetate or bisacetonitrilepalladium chloride. Particular preference is given to using palladium chloride.

In general, from 6 to 60, preferably from 15 to 25, equivalents of the aforementioned complex ligands, in particular triphenylphosphine and tri-tert-butylphosphine, are combined with one equivalent of the palladium salt.

EP-A 0 888 261 describes the use of from 2 to 6 equivalents of triphenylphosphine per equivalent of the palladium catalyst. The use of high ligand excesses is generally viewed in the literature as disadvantageous, since this is expected to result in inactivation of the catalytically active complex (cf., for example, J. Hassan et al., Chem. Rev. 2002, 102, 1359). It was thus surprising that this high triphenylphosphine use in combination with the low catalyst use led to an increase in the overall yield of the process of the present invention and accordingly to an improvement in the economic viability. Metallic palladium is used preferably in pulverized form or on a support material, for example in the form of palladium on activated carbon, palladium on alumina, palladium on barium carbonate, palladium on barium sulfate, palladium on calcium carbonate, palladium aluminosilicates such as montmorillonite, palladium on $SiO_2$ and palladium on calcium carbonate, in each case with a palladium content of from 0.5 to 12% by weight. In addition to palladium and the support material, these catalyst may comprise further dopants, for example lead.

When metallic palladium optionally applied to support is used, particular preference is given to also using the aforementioned complex ligands, in particular to the use of palladium on activated carbon in the presence of triphenylphosphine as a complex ligand, where the phenyl groups in the triphenylphosphine are preferably substituted by a total of from one to three sulfonate groups. In the process according to the invention, the palladium catalyst is used with a low fraction of from 0.001 to 1.0 mol %, preferably from 0.005 to 0.5 mol % or from 0.01 to 0.5 mol % and in particular from 0.005 to 0.05 mol %, based on the amount of compound (II)

The low use of a palladium salt in combination with a high use of a complex ligand constitutes a significant cost advantage of this process over the prior art processes.

The process according to the invention may be carried out in a biphasic system composed of aqueous phase and solid phase, i.e. the catalyst. In that case, the aqueous phase may also comprise a water-soluble organic solvent in addition to water.

Organic solvents suitable for the process according to the invention are ethers such as dimethoxyethane, diethylene glycol dimethyl ether, tetrahydrofuran, dioxane and tert-butyl methyl ether, hydrocarbons such as n-hexane, n-heptane, cyclohexane, benzene, toluene and xylene, alcohols such as methanol, ethanol, 1-propanol, 2-propanol, ethylene glycol, 1-butanol, 2-butanol and tert.-butanol, ketones such as acetone, ethyl methyl ketone and isobutyl methyl ketone, amides such as dimethylformamide, dimethylacetamide and N-methylpyrrolidone, in each case individually or in a mixture.

Preferred solvents are ethers such as dimethoxyethane, tetrahydrofuran and dioxane, hydrocarbons such as cyclohexane, toluene and xylene, alcohols such as ethanol, 1-propanol, 2-propanol, 1-butanol and tert.-butanol, in each case individually or in a mixture. In a particularly preferred variant of the process according to the invention, water, one or more water-insoluble and one or more water-soluble solvents are used, for example mixtures of water and dioxane, or water and tetrahydrofuran, or water, dioxane and ethanol, or water, tetrahydrofuran and methanol, or water, toluene and tetrahydrofuran, preferably water and tetrahydrofuran, or water, tetrahydrofuran and methanol.

The total amount of solvent is normally from 3000 to 500 g and preferably from 2000 to 700 g, per mole of the compound (II).

Appropriately, the process is carried out by adding the compound (II), the organoboron compound (III), the base and the catalytic amount of the palladium catalyst to a mixture of water and one or more inert organic solvents, and stirring at a temperature of from 20° C. to 100° C., preferably from 50° C. to 90° C., more preferably from 60° C. to 80° C., for a period of from 1 to 50 hours, preferably from 2 to 24 hours.

Depending on the solvent and temperature used, a pressure of from 1 bar to 6 bar, preferably from 1 bar to 4 bar, is established. Preference is given to carrying out the reaction in water and tetrahydrofuran. The reaction may be carried out in customary apparatus suitable for such processes. On completion of reaction, palladium catalyst obtained as a solid is removed, for example by filtration, and the crude product is freed from the solvent or the solvents. In the case of products which are not fully water-soluble, water-soluble palladium catalysts or complex ligands are removed fully from the crude product in the separation of the water phase. Subsequently, further purification may be effected by methods which are known to those skilled in the art and are appropriate to the particular product, for example by recrystallization, distillation, sublimation, zone melting, melt crystallization or chromatography.

By the process according to the invention, it is possible to prepare, for example:
3',4'-dichloro-5-fluoro-N-(propan-2-ylidene)biphenyl-2-amine, 3',4'-dichloro-N-(propan-2-ylidene)biphenyl-2-amine, 4'-chloro-N-(propan-2-ylidene)biphenyl-2-amine, N-(3',4'-dichloro-5-fluorobiphenyl-2-yl)acetamide, N-(4'-chloro-5-fluorobiphenyl-2-yl)acetamide, N-(3',4'-dichlorobiphenyl-2-yl)acetamide.

The process according to the invention affords the compounds I in very high up to quantitative yields at very good purity. The substituted biphenyls obtainable by the process according to the invention are suitable as precursors for fungicidal crop protection active ingredients (cf. WO

PREPARATION EXAMPLES

1. Preparation of (3,4-Dichlorophenyl)boronic acid 100 kg tetrahydrofurane and 6 kg magnesium turnings were added to a reaction vessel under nitrogen at room temperature. 10-20 kg of bromo(3,4-dichlorophenyl)magnesium which were freshly prepared before use and, subsequently, 15 kg of a 18% solution of 4-bromo-1,2-dichlorobenzene in THF were charged. When an exotherm is observed, addition the 4-bromo-1,2-dichlorobenzene solution was continued (293 kg) maintaining the temperature below 50° C. After addition, the reaction mixture was stirred overnight at room temperature.

After cooling the reaction mixture at −10° C., 25 kg trimethyl borate were added to the reaction mixture. After 30 minutes of post-stirring, the reaction mixture was allowed to warm to 20° C. and stirred for two hours at this temperature.

To the reaction mixture 230 kg 10% sulfuric acid were added maintaining the temperature in a range of −10° C. to −5° C. After end of addition, the mixture was allowed to warm to 20° C. and stirred for two hours. 400 kg water were charged. The aqueous layer was separated off.

(3,4-Dichlorophenyl)boronic acid was obtained in 70-80% yield which was determined by HPLC analysis of the organic phase. This phase can be directly used in the following Suzuki cross-coupling step.

2. Synthesis of Bis(3,4-dichlorophenyl)borinic acid

To a dry flask was added tribromoborane in DCM (13 ml, 13 mmol, 1M). This solution was cooled to −62° C., and bromo(3,4-dichlorophenyl)magnesium (50 ml, 25 mmol, 0.5M in THF) was added dropwise to the cold solution. The reaction mixture was allowed to warm to room temperature and stirred over night. The solvent was removed in vacuo, and the residue was dissolved in DCM and hydrolyzed by the slow addition of 1N HCl. The organic layer was separated and washed with brine, and the solvent was removed in vacuo. The resulting oil was purified by silica gel chromatography using 25% ethyl acetate as the eluent, which afforded the title compound as a solid (3.34 g, 10.4 mmol, 80% yield).

3. Synthesis of N-(3',4'-dichloro-5-fluorobiphenyl-2-yl)acetamide

Under argon atmosphere, a suspension of N-(2-bromo-4-fluorophenyl)acetamide (1.00 g, 4.27 mmol), bis(3,4-dichlorophenyl)borinic acid (0.685 g, 2.14 mmol), potassium carbonate (1.03 g, 7.44 mmol), [(t-Bu)$_3$PH]BF$_4$ (1.5 mg, 5 mmol), Pd(acac)$_2$ (1.6 mg, 5 5 mmol) in 8 ml water and 2 ml 1-butanol was heated to 60° C. The reaction mixture was stirred at 60° C. for about 13 h, cooled to room temperature and acidified with 1N HCl. The mixture was extracted twice with ethyl acetate and the organic layer was dried over MgSO$_4$. The solvent was removed under vacuo. After drying 1.22 g raw product was obtained (80.5% GC-MS-purity, 77% yield).

03/070705). In most cases the amine protection group will be removed before further converting the amines.

What is claimed is:

1. A process for preparing a substituted biphenylanilide of formula (I),

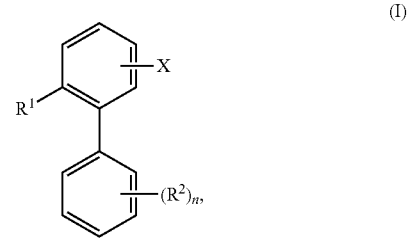

wherein
X is hydrogen, fluorine or chlorine;
$R^1$ is —NH(CO)$R^3$ or —N=C$R^4R^5$; and
$R^3$, $R^4$, $R^5$ independent from each other represent hydrogen, —C$_2$—(C=O)CH$_3$, $C_1$-$C_8$-alkyl, $C_1$-$C_8$-alkenyl, $C_1$-$C_8$-alkynyl or $C_6$-$C_{18}$-aryl; or
$R^4$, $R^5$ together with the carbon atom to which they are attached form a five- or six-membered ring comprising one, two or three hetero atoms selected from the group consisting of N, O, and S;
$R^2$ is cyano, nitro, halogen, $C_1$-$C_6$-alkyl, $C_1$-$C_6$-alkenyl, $C_1$-$C_6$-alkynyl, $C_1$-$C_6$-alkoxy, $C_1$-$C_6$-haloalkyl, ($C_1$-$C_6$-alkyl)carbonyl or phenyl; and
n is 1, 2 or 3, where in case that n is 2 or 3, the $R^2$ radicals may also be different,
which comprises reacting a compound of formula (II)

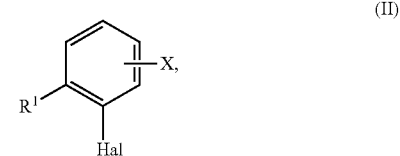

in which Hal is halogen and X is as defined above, in the presence of a base and a palladium catalyst selected from the group consisting of:
a) palladium-triarylphosphine or -trialkylphosphine complex with palladium in the zero oxidation state,
b) salt of palladium in the presence of triarylphospine or trialkylphosphine as a complex ligand, and
c) metallic palladium, optionally applied to support, in the presence of triarylphosphine or trialkylphosphine;
in a solvent, with an organoboron compound of formula (III)

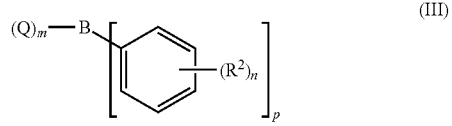

selected from the group consisting of:
(i) a boronic acid of formula (III)
wherein
m is 2,
each Q is a hydroxyl-group,
$R^2$ and n are as defined above,
or the anhydrides, dimers or trimers formed thereof;

(ii) a boronic acid derivative of formula (III), wherein
m is 2,
p is 1,
each Q is independently selected from the group consisting of F, Cl, Br, I, $C_{1-4}$-alkyl-, $C_{6-10}$-aryl, $C_{1-4}$-alkoxy- and $C_{6-10}$-aryloxy-residues,
$R^2$ and n are as defined above;
(iii) a bonnie acid of formula (III),
wherein
m is 1,
p is 2,
Q is selected from the group consisting of OH, F, Cl, Br, I, $C_{1-4}$-alkyl-, $C_{6-10}$-aryl-, $C_{1-4}$-alkoxy- and $C_{6-10}$-aryloxy-residues,
$R^2$ and n are as defined above;
(iv) a cyclic boronic acid ester of formula (III),
wherein
m is 2,
p is 1,
each Q is independently $C_{1-4}$-alkoxy residues which together with the boron atom they are attached form a 5- or 6-membered ring which may be substituted by $C_{1-4}$-alkyl-residues,
$R^2$ and n are as defined above;
(v) a boronate of formula (III)
wherein
m is 3,
p is 1,
$R^2$ and n are as defined above;
each Q is independently selected from the group consisting of OH, F, Cl, Br, I, $C_{1-4}$-alkyl-, $C_{6-10}$-aryl-, $C_{1-4}$-alkoxy- and $C_{6-10}$-aryloxy-residues,
and wherein the negative charge of the boronate anion is compensated by a cation;
(vi) a triarylborane of formula (III),
wherein
m is 0,
p is 3,
$R^2$ and n are as defined above; and
(vii) a tetraarylborate of formula (III),
wherein
m is 0,
p is 4,
$R^2$ and n are as defined above,
and wherein the negative charge of the boronate anion is compensated by a cation; and
where the triarylphosphines or trialkylphosphines used may optionally be substituted.

2. The process according to claim 1, wherein the compound (II) is selected from the group consisting of N-(2-bromo-4-fluorophenyl)acetamide, N-(2-chloro-4-fluorophenyl)acetamide, N-(2-bromo-phenyl)acetamide, N-(2-chlorophenyl)acetamide, N-(2-chlorophenyl)-3-oxobutanamide, N-(2-bromophenyl)-3-oxobutanamide, N-(2-chloro-4-fluorophenyl)-3-oxobutanamide, N-(2-bromo-4-fluorophenyl)-3-oxobutanamide, 2-bromo-N-(propan-2-ylidene)aniline, 2-chloro-N-(propan-2-ylidene)aniline, 2-bromo-4-fluoro-N-(propan-2-ylidene)aniline, and 2-chloro-4-fluoro-N-(propan-2-ylidene)aniline.

3. The process according to claim 1, wherein the starting compound (III) is a diphenylborinic acid which is substituted in the 3- and 4-position.

4. The process according to claim 3, wherein the diphenylborinic acid (III) bears fluorine or chlorine in the 3- and 4-positions.

5. The process according to claim 4, wherein the compound of formula (III) is di(3,4-dichlorophenyl)borinic acid.

6. The process according to claim 1, wherein the palladium catalyst a) according to claim 1 used is tetrakis(triphenylphosphine)palladium or tetrakis(tri-tert.-butylphosphine)palladium.

7. The process according to claim 1, wherein a palladium catalyst b) is used.

8. The process according to claim 1, wherein the palladium catalyst c) used is metallic palladium on activated carbon in the presence of triphenylphosphine wherein the phenyl groups in triphenylphosphine are substituted by a total of from 1 to 3 sulfonate groups.

9. The process as claimed in claim 7, wherein the salt of the palladium catalyst b) used is palladium chloride, palladium acetate or bisacetonitrilepalladium chloride.

10. The process according to claim 7, wherein from 6 to 60 equivalents of triphenylphosphine are used per equivalent of the palladium salt.

11. The process according to claim 1, wherein from 0.001 to 1.0 mol % of the palladium catalyst is used, based on the amount of the compound of formula (II).

12. The process according to claim 1, wherein the reaction is carried out at a temperature of from 20 to 80° C.

13. The process according to claim 1, wherein the reaction is carried out in a mixture of water and an organic solvent.

14. The process according to claim 1, wherein the organic solvent used is an ether.

* * * * *